US005489777A

United States Patent [19]
Stedman et al.

[11] Patent Number: 5,489,777
[45] Date of Patent: Feb. 6, 1996

[54] APPARATUS FOR REMOTE ANALYSIS OF VEHICLE EMISSIONS USING REFLECTIVE THERMOGRAPHY

[75] Inventors: Donald H. Stedman, Denver; Gary A. Bishop, Louisville, both of Colo.

[73] Assignee: Denver Seminary, Denver, Colo.

[21] Appl. No.: 398,359

[22] Filed: Mar. 3, 1995

Related U.S. Application Data

[63] Continuation-in-part of Ser. No. 253,749, Jun. 3, 1994, Pat. No. 5,401,967, which is a continuation-in-part of Ser. No. 895,342, Jun. 8, 1992, Pat. No. 5,319,199, which is a continuation-in-part of Ser. No. 633,952, Dec. 26, 1990, Pat. No. 5,210,702.

[51] Int. Cl.$^6$ ............................ G01N 21/01; G01N 21/17
[52] U.S. Cl. ............... 250/338.5; 250/330; 250/339.13; 250/342
[58] Field of Search .................... 250/338.5, 330, 250/342, 338.1, 339.13

[56] References Cited

U.S. PATENT DOCUMENTS

| | | |
|---|---|---|
| 3,958,122 | 5/1976 | Jowett et al. . |
| 3,973,848 | 8/1976 | Jowett et al. . |
| 4,160,373 | 7/1979 | Fastaia et al. . |
| 4,348,732 | 9/1982 | Kreft . |
| 4,432,316 | 2/1984 | Ogita . |
| 4,924,095 | 5/1990 | Swanson, Jr. ............... 250/338.5 |
| 5,002,391 | 3/1991 | Wolfrum et al. . |
| 5,210,702 | 5/1993 | Bishop et al. ............... 250/338.5 X |
| 5,255,511 | 10/1993 | Maus et al. . |
| 5,307,626 | 5/1994 | Maus et al. . |
| 5,319,199 | 6/1994 | Stedman et al. ............... 250/338.5 |
| 5,401,967 | 3/1995 | Stedman et al. ............... 250/338.5 |

OTHER PUBLICATIONS

Barnes Engineering Company, "Barnes Infrared Camera", Bulletin 12–600, pp. 1–12.

"Automobile Carbon Monoxide Emission" Environmental Science Technology, v. 23, pp. 147–149, 1989.

"IR Long–Path Photometry: A Remote Sensing Tool for Automobile Emissions", Analytical Chem., v. 61, pp. 671A–676S, 1989.

"The Remote Measurement of Traffic Generated Carbon Monoxide", J. Air Pollution Control Association, v. 33, pp. 220–222, 1983.

*Primary Examiner*—Carolyn E. Fields
*Assistant Examiner*—Edward J. Glick
*Attorney, Agent, or Firm*—Dorr, Carson, Sloan & Birney

[57] ABSTRACT

A system for remote analysis of vehicle emissions also determines whether each vehicle's engine and exhaust system are hot or cold by measuring infrared radiation reflected by the roadway beneath the vehicle. A source transmits a beam of radiation through at least a portion of the motor vehicle exhaust to a number of sensors. Each sensor generates a signal indicative of the absorption of the beam in a wavelength band indicative of a corresponding exhaust gas (e.g., CO, $CO_2$, HC, $NO_x$ and $H_2O$). An infrared detector measures infrared radiation within a field of view including at least a portion of the roadway beneath each passing vehicle. A processor then computes the concentrations of each exhaust gas from the sensor signals, and determines whether the vehicle is hot or cold by measuring the intensity of infrared radiation detected by the infrared detector. Because cold vehicles can temporarily produce abnormally high pollution emissions, the processor can be programmed to separately identify hot vehicles having exhaust emissions that exceed air pollution limits. The system can also include a video camera and recorder to record the license plate and emissions data for each vehicle identified as failing to meet emissions limits.

25 Claims, 14 Drawing Sheets

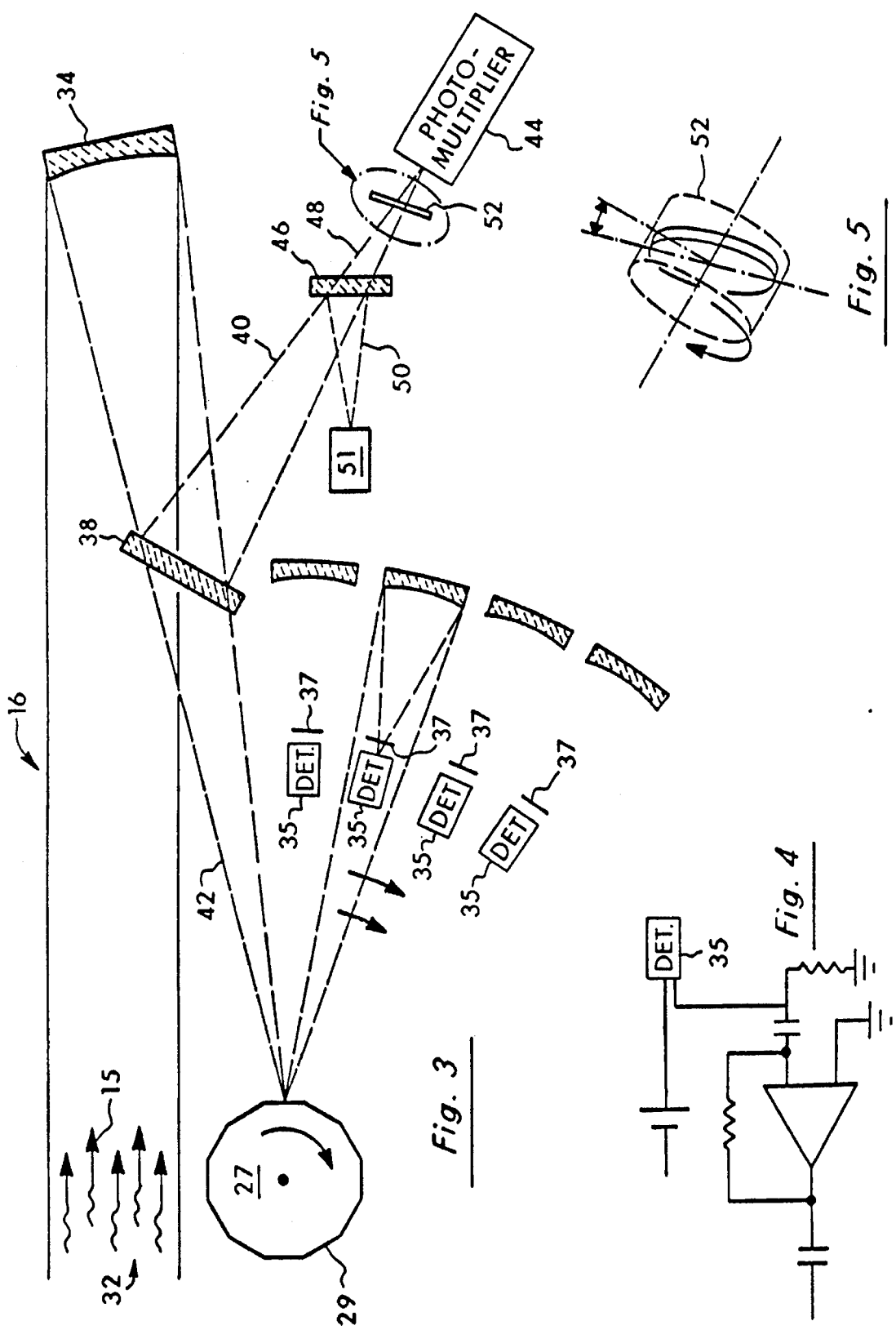

APPARATUS FOR REMOTE ANALYSIS OF VEHICLE EMISSIONS USING REFLECTIVE THERMOGRAPHY

RELATED APPLICATION

The present application is a continuation in part of the Applicants' U.S. patent application Ser. No. 08/253,749, entitled "Apparatus for Remote Analysis of Vehicle Emissions," filed on Jun. 3, 1994, now U.S. Pat. No. 5,401,967, issued on Mar. 28, 1995, which is a continuation in part of U.S. patent application Ser. No. 07/895,342, filed on Jun. 8, 1992, now U.S. Pat. No. 5,319,199, issued on Jun. 7, 1994, which was a continuation in part of U.S. patent application Ser. No. 07/633,952, filed on Dec. 26, 1990, now U.S. Pat. No. 5,210,702, issued on May 11, 1993.

BACKGROUND OF THE INVENTION

Federal and state governments, along with vehicle manufacturers, test and certify new vehicle emissions, and also carry out some in-use testing of older vehicles. These tests comply with the Federal Test Procedure (FTP) as outlined in the Federal Register, which is a carefully designed and specified three-phase test under "cold transient," "cold stabilized," and "hot transient" conditions. The vehicle is generally driven in a series of accelerations, decelerations, stops, and starts on a chassis dynamometer, whose inertia and friction are specifically set for each vehicle. The emissions from each phase are collected at a constant volume into a sample bag, and the concentrations of each species of pollutant are determined from the integration of the entire bag, with a final result given in grams of pollutant per mile.

The driving course is modeled after a "typical" summertime commute to work in Los Angeles. Each of these tests takes at least twelve hours to complete and costs in excess of about $700, in 1990 dollars. The reproducibility of the results for a given vehicle is believed to be plus or minus 20%, controlled mainly by the repeatability of the vehicle emissions system and not by the test system or gas analysis protocols. Presently available computer models are based on the concept that the FTP emissions measured from a fleet of vehicles are well correlated, although not necessarily one to one, with the emissions that the same fleet would exhibit under in-use driving conditions. However, since very little is known about actual on-the-road fleet emissions, it is impossible to truly gauge the accuracy of this assumption.

In addition to any new car emission certification programs, there are also state inspection and maintenance (IM) programs designed to test every vehicle in a given area that are, therefore, much less rigorous tests. Most sophisticated centralized IM testing programs use a very much shorter FTP-type test on a chassis dynamometer, or one or two fixed loads and speeds, and measure the steady-state emissions as a percentage of the exhaust. Many centralized, and all current decentralized programs measure only idle emissions as a percentage of the exhaust at one, or possibly two, engine speeds.

In late 1986, a fuel efficient automobile test (FEAT) system was developed and designed to remotely detect carbon monoxide and carbon dioxide levels in vehicular emissions and to make specific measurements on individual vehicles. This system is more specifically described in an article entitled "*Automobile Carbon Monoxide Emission,*" Environmental Science Technology, vol. 23, pages 147–149, 1989. Also see "*IR Long-Path Photometry: A Remote Sensing Tool for Automobile Emissions,*" Analytical Chem., vol. 61, pages 671A–676A, 1989. This particular device, while extremely accurate, had its limitations in that it was unable to identify the specific vehicles found to be emitting carbon monoxide in excess of acceptable levels so that the vehicle owner could be subsequently contacted and advised to adjust or repair or modify the vehicle to control its emissions. Moreover, while it was capable of measuring carbon monoxide and carbon dioxide, it was not capable of measuring other emission components or the temperature at which the vehicle was operating, the knowledge of which would be extremely valuable to have.

As indicated, it is known to the inventors that the basic idea of remotely measuring vehicle emissions is not a new one. Lockheed Missiles and Space Corporation first attempted construction of an across-the-road monitor, the successful operation of which was never published. L. Chaney, "The Remote Measurement of Traffic Generated Carbon Monoxide," *J. Air Pollution Control Association* (vol. 33, pages 220–222, 1983) proved that carbon monoxide fumes (and only carbon monoxide) from passing vehicles could be observed in real-time with a gas filter correlation radiometer. However, Chaney's system did not include any of the parameters required to accurately measure emissions data from vehicle exhaust plume observations.

It is also well known that vehicle exhaust emissions change as a function of the operating temperature of the vehicle engine and exhaust system. When a vehicle is first started, its engine and exhaust system are often in a relatively cold state that leads to incomplete combustion in the engine cylinders and less than optimal performance of the catalytic converter and other components of the exhaust system in controlling pollutants in the exhaust. As the engine and exhaust system gradually warm during operation, the chemical composition of the vehicle exhaust will gradually shift to values that more accurately reflect steady-state operation of the vehicle. Emissions data from cold vehicles are inherently high and therefore tend to be an unreliable indicator of the vehicle's overall emissions levels. Relatively high levels of emissions from a cold vehicle may falsely identify the vehicle as a gross polluter, when in fact, the vehicle's emissions levels are within acceptable limits after the vehicle has warmed up to its normal operating condition. This problem has been identified in other systems for measuring and controlling vehicle emissions, as follows:

| Inventor | U.S. Pat. No. | Issue Date |
| --- | --- | --- |
| Jowett et al. | 3,958,122 | May 18, 1976 |
| Jowett et al. | 3,973,848 | Aug. 10, 1976 |
| Fastaia et al. | 4,160,373 | July 10, 1979 |
| Kreft | 4,348,732 | Sept. 7, 1982 |
| Ogita | 4,432,316 | Feb. 21, 1984 |
| Wolfrum et al. | 5,002,391 | Mar. 26, 1991 |
| Maus et al. | 5,255,511 | Oct. 26, 1993 |
| Maus et al. | 5,307,626 | May 3, 1994 |

Jowett et al. disclose an exhaust gas analyzer having pressure and temperature compensation. The exhaust gas emissions are fed into a sample cell 28 having a thermister 40 to measure the temperature the exhaust gas. This system is apparently intended to measure exhaust emissions from a stationary vehicle and would not be suitable for measuring emissions from a series of moving vehicle on a roadway under actual driving conditions.

Fastaia et al. and Kreft disclose other examples of exhaust gas analyzers for measuring emissions from a stationary vehicle. Again, a thermistor is employed to measure the temperature of the exhaust gas passing through a sample cell.

Ogita discloses an apparatus for controlling hydrocarbon emissions from automobiles equipped with a catalytic converter while the engine is cold.

Wolfrum et al. disclose a gas analysis system for flue gases exhausted from power plants and industrial facilities. A temperature detector 37, such as a radiation pyrometer, is used to measure the temperature of the flue gases.

Maus et al. disclose a system for operational monitoring of a catalytic converter of the exhaust system of an engine. The temperature of the walls of the catalytic convertor is measured for at least two regions within the catalytic converter. This information is used to control operation of the engine.

None of the prior art systems are capable of remotely measuring the temperature of moving vehicles on a roadway under actual operating driving conditions. Therefore, a need exists for a system to remotely determine vehicle temperature in order to validate or invalidate emission measurements for each vehicle.

SUMMARY OF THE INVENTION

A system for remote analysis of vehicle emissions also determines whether each vehicle's engine and exhaust system are hot or cold by measuring infrared radiation reflected by the roadway beneath the vehicle. A source transmits a beam of radiation through at least a portion of the motor vehicle exhaust to a number of sensors. Each sensor generates a signal indicative of the absorption of the beam in a wavelength band indicative of a corresponding exhaust gas (e.g., CO, $CO_2$, HC, $NO_x$ and $H_2O$). An infrared detector measures infrared radiation within a field of view including at least a portion of the roadway beneath each passing vehicle. A processor then computes the concentrations of each exhaust gas from the sensor signals, and determines whether the vehicle is hot or cold by measuring the intensity of infrared radiation detected by the infrared detector. Because cold vehicles can temporarily produce abnormally high pollution emissions, the processor can be programmed to separately identify hot vehicles having exhaust emissions that exceed air pollution limits. The system can also include a video camera and recorder to record the license plate and emissions data for each vehicle identified as failing to meet emissions limits.

A primary object of the present invention to provide an improved remote gas analysis system for accurately identifying vehicles having excessive pollutant emissions by distinguishing between hot and cold vehicles in addition to measuring exhaust emission levels.

It is another object of the present invention to provide an emissions detection system capable of remotely measuring emissions and operating temperatures of moving vehicles under actual driving conditions.

It is yet another object of the present invention to provide an emissions detection system for recording images of the license plate of vehicles identified as having excessive pollutant emissions, together with emissions data measured for the vehicle.

BRIEF DESCRIPTION OF THE DRAWINGS

The accompanying drawings illustrate complete preferred embodiments of the present invention and the best modes presently devised for the practical application of the principles thereof, in which:

FIG. 3 is a schematic diagram of one preferred embodiment of a detector unit 16 for use in the remote measuring and monitoring system of the present invention.

FIG. 4 is a schematic diagram of a circuit for use in the infrared detectors of the present invention.

FIG. 5 is a schematic diagram of a tilting filter for use in the ultraviolet detection of $NO_x$.

DETAILED DESCRIPTION OF THE INVENTION

Figure 1:
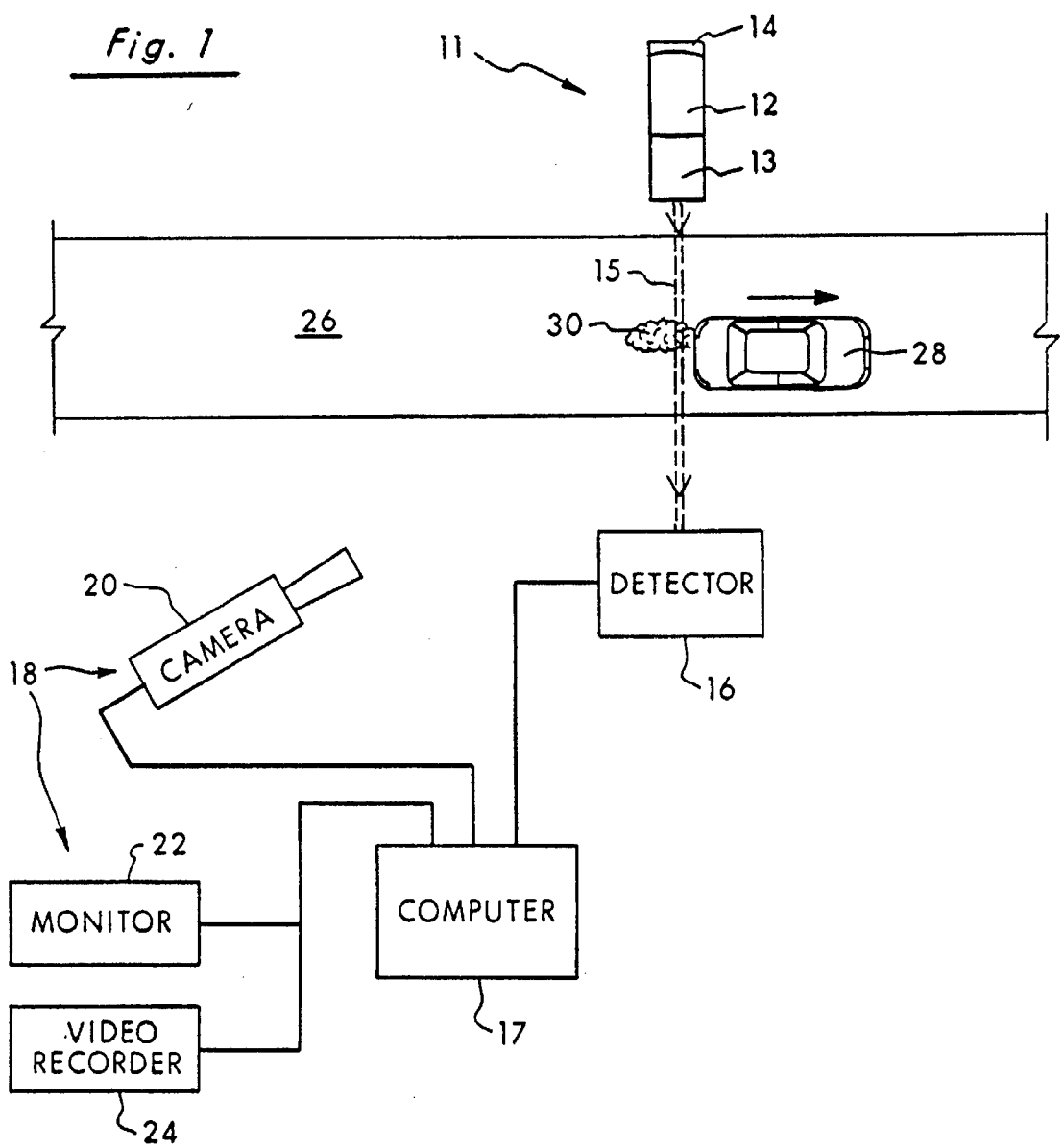
FIG. 1 is a schematic diagram of the remote measuring and monitoring system of the present invention shown in use across a roadway with one vehicle and its exhaust in a detection position.

Referring now to FIG. 1, the system includes a light source 11 made up of an ultraviolet radiation source 12, an infrared radiation source 13, a device 14 for collimating the light beams from the sources 12 and 13 into a collimated beam 15, a detector unit 16 having a computer 17, and a video monitoring system 18. The video monitoring system 18 preferably includes a video camera 20, a monitor unit 22, and a video recording storage device 24. The ultraviolet radiation source 12 and infrared radiation source 13 may be collimated, and therefore not require collimating device 14.

The present invention utilizes infrared absorption to measure the concentrations of carbon monoxide, carbon dioxide, hydrocarbons, and water added to the air by an individual passing vehicle. In addition, the system can utilize ultraviolet absorption to determine the concentration of nitrogen oxides added to the air by such a vehicle. In one embodiment, the light source 11 is located on one side of an open space, typically a roadway 26, along which a vehicle 28 moves. The light source 11 sends a collimated beam of radiation 15 into the detector unit 16 on a continuous basis. A computer 17 continuously samples all infrared and ultraviolet beam intensities received by each of the sensors of the detector unit 16. When the beam 15 is blocked by a vehicle 28 as it passes along the roadway 26, the memory of the computer 17 retains information concerning the carbon monoxide, carbon dioxide, hydrocarbons, nitrogen oxides, and water levels in the ambient atmosphere in front of the vehicle 28 prior to the blocking of the beam 15, and then samples the carbon monoxide, carbon dioxide, hydrocarbons, nitrogen oxides, and water levels of the exhaust 30 behind the vehicle 28 for a predetermined period (e.g., about 0.1 to about 1.0 second) after resumption of reception of the beam 15 by the detector unit 16.

In one preferred embodiment, a vehicle-identifying system, such as a video camera 20, records the end view portion of the vehicle 28 (including the vehicle's license plate) simultaneously with the unblocking of the beam 15 by the vehicle 28. This is generally the rear portion of the vehicle 28, although the front or other portions of the vehicle can be recorded. When the vehicle 28 has passed the detector 16 and the exhaust 30 has been sampled, the results are compared to the carbon monoxide, carbon dioxide, hydrocarbons, nitrogen oxides, and water levels recorded prior to beam interruption, as well as to calibration plots stored in computer memory. The carbon monoxide, carbon dioxide, hydrocarbons, nitrogen oxides, and water emission levels are then displayed on the monitor 22 along with a stop-frame video image of the vehicle 28 in relation to the date and time of the emissions measurement. This is then permanently stored on magnetic media by video recorder 24. Any type of storage unit 24 may be utilized with the invention including digital image storage and the like. Thus, the carbon monoxide, carbon dioxide, hydrocarbons, nitrogen oxides, and water emissions of the vehicle 28 are remotely sensed, and an identifying image of the vehicle, such as a stop-frame video, is overlaid by the date, time, the number of the vehicle in a series of vehicles (if desired), and the various emission levels, while also simultaneously permitting real-time reading of the data at the monitor 22. The computer system 17 may be designed to actually read the vehicle license plate using currently available optical character recognition software, or the operator of the system may read the information from the monitor 22 and then type this information and the license plate number into a computer data base. If the computer 17 or associated equipment is on-line with the Department of Motor Vehicles license registration data bank, the vehicle type, model, and year can also be displayed in the video image, along with the mandatory, if any, emission requirements of the state. In this manner, a particular vehicle could be identified as complying or not complying with state emission requirements immediately at the time and site of measurement, or at a later time if desired.

In more particular reference to FIG. 1, any available ultraviolet and infrared radiation source may be utilized with the present invention, along with a mechanism for directing the radiation beam 15 across the roadway 26. In the present invention, a preferred infrared radiation source 13 includes a commercial gas dryer ignitor, General Electric number WE4X444. A preferred ultraviolet radiation source includes a deuterium arc lamp or xenon arc lamp 12 emitting ultraviolet radiation therefrom. One manner of directing the ultraviolet and infrared radiation beams from the sources 12 and 13, respectively, includes the use of a reflective mirror 14 to direct the collimated beam of infrared radiation from the infrared source 13 across the roadway 26. A dichroic mirror or prism is provided in the form of a mirror 19 through which infrared radiation from the infrared source 13 passes so as to blend with the reflected ultraviolet beam to form a combined collimated beam 15. Another preferred embodiment of the present invention includes the use of a narrow angle CaF prism, with the sources 12 and 13 positioned at appropriate angular alignments to the prism so that a combined collimated beam 15 is emitted therefrom. With such a prism, the infrared radiation is hardly bent when passing therethrough, although the ultraviolet radiation is bent at a considerable angle. The appropriate arrangement of the sources 12, 13 relative to such a prism (not illustrated) would enable the ultraviolet beam to be exactly combined with the infrared beam in the collimated beam 15.

Figure 2:
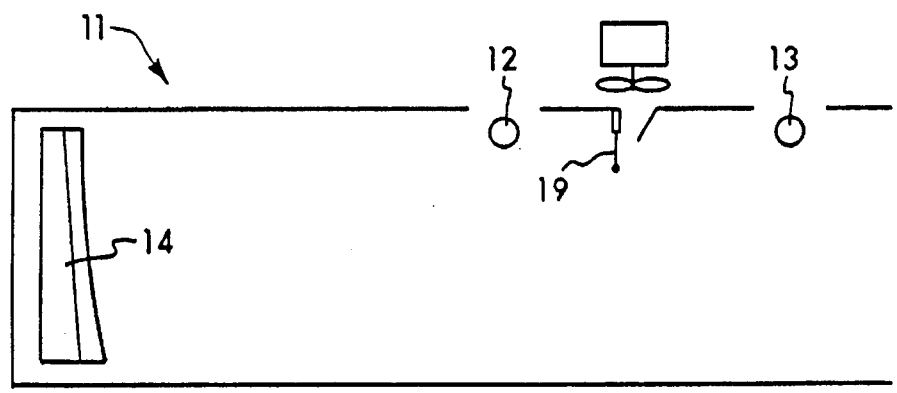
FIG. 2 is a schematic diagram of one preferred embodiment of a light source 11 for use in the remote measuring and monitoring system of the present invention.

A second, and more preferred, embodiment of the present invention is illustrated in FIG. 2, which illustrates the use of a dichroic mirror 19, which reflects ultraviolet radiation and passes infrared radiation.

With more particular reference to FIG. 3 and one preferred embodiment of the detector unit 16, an opening area 32 is provided for receiving the collimated beam 15. The opening area 32 is arranged such that as the collimated beam 15 enters therethrough, it is focused by an adjustable mirror 34 onto a beam splitter 38 (e.g., a beam splitter composed of CaF and appropriate overcoatings). While not shown, a CaF prism may also be utilized to divide the collimated beam 15 into two beams, one ultraviolet beam 40 and one infrared beam 42. As previously indicated, using a CaF narrow angle prism, infrared is hardly bent while the ultraviolet is bent at a considerable angle. Thus, the prism functions as a beam splitter to divide the ultraviolet and infrared portions from the collimated beam 15. The ultraviolet beam 40 is directed to an ultraviolet photomultiplier device 44 that functions to measure the absorption of ultraviolet in the roadway 26 exterior to the detector unit 16.

In the illustrated embodiment, an additional beam splitter 46 is provided to divide the ultraviolet beam 40 into two components, one component 48 being directed onto the photomultiplier 44 while another component 50 is directed onto a second photodetector 51 used for measuring background radiation. In one preferred form, a tilting interference filter 52 mounted at an angle on a rapidly rotating shaft is employed to generate a DC electrical signal in the absence of $NO_x$, but provides an AC electrical signal in the presence of $NO_x$. With AC coupled electronics, only $NO_x$ is observed by the photomultiplier device 44. The photomultiplier unit 44 is designed to provide a first electrical signal indicative of the absorption of ultraviolet radiation from the collimated beam 15 by the vehicle exhaust 30.

Now, with more particular reference to FIGS. 2 and 3, the detector unit 16, with an opening area 32 is provided to observe across a road 26 across which is transmitted infrared radiation and ultraviolet radiation in a single beam 15. Beam 15 is created using two separate light sources, infrared radiation from source 13 and ultraviolet radiation from source 12. The infrared and ultraviolet radiation are combined into the single beam 15 by a dichroic mirror 19. The dichroic mirror 19 is overcoated for ultraviolet radiation reflection, and passes infrared radiation, thereby passing infrared radiation and reflecting ultraviolet radiation. In the detector unit 16, the beam 15 is split into ultraviolet radiation 40 and infrared radiation 42 by a substantially identical dichroic mirror 38. The ultraviolet radiation 40 is then detected with an appropriate interference filter 52 and photomultiplier tube 44, as described above.

The infrared beam 42 continues through the detector unit 16 and is directed onto a rotating mirrored surface 27, for example, a rotating polygon structure such as a dodecagon having reflective mirrors 29 covering each of its sides. The rotating mirrored surface 27 reflects the beam 42 to each of the infrared photodetectors 35 in sequence. It should be noted that the rotating reflector 27 serves to time-multiplex the beam 42 to each of the photodetectors 35. In other words, given a system with N photodetectors, each photodetector receives essentially the full intensity of the infrared beam 42 during 1/Nth of any temporal period. Due to the performance characteristics of typical infrared photodetectors, it has been found that time-multiplexing results in greater sensitivity and accuracy than if each photodetector receives 1/Nth of the intensity of the infrared beam at all times.

A separate sensor assembly is provided for each chemical species in the exhaust to be monitored. Each sensor assembly consists of a photodetector 35 and a filter 37 selected to pass a wavelength indicative of the chemical species being monitored by the particular sensor assembly. For example, a filter 37 having a wavelength of 3.9 microns can be used for the reference channel, 4.3 microns for $CO_2$, 4.6 microns for CO, and 3.3–3.4 microns for hydrocarbons. For example, a liquid nitrogen-cooled indium antimonide photovoltaic detector or a lead selenide detector operated at or below ambient temperature can be used for each of the infrared detectors 35.

Referring back to the ultraviolet beam 40 and the photomultiplier unit 44, $NO_x$ in the predominantly emitted form of nitric oxide, NO, is measured by making use of the ultraviolet absorption in the wavelength range of about 230 nm. The use of ultraviolet absorption for NO has several advantages. These advantages include an ultraviolet absorption coefficient about 1000 times larger than an infrared absorption coefficient, giving rise to larger signals. Moreover, there is no interference from water vapor in the ultraviolet. The atmosphere is optically transparent, but ultraviolet radiation from the sun is irrelevant because the stratospheric ozone layer cuts out substantially all of the ultraviolet radiation. Finally, solar-blind ultraviolet-detecting photomultiplier tubes as utilized in the unit 44 are available that are very sensitive and stable. This means that very low (i.e., eye safe) levels of ultraviolet radiation can be used for detection in the detector unit 16.

In operation, the detector unit 16 is set up preferably along a single-lane highway with the collimated ultraviolet and infrared beam 15 located approximately 10 inches above the roadway. The computer 17 monitors the infrared and ultraviolet signal intensities of the reference channel, and the signals are optimized by alignment of the source 11 and the detector unit 16. Upon entry of a vehicle 28 into the optical path of the beam 15, a drop in the voltage from the reference channel signals the presence of the vehicle 28. Voltages from each of the other signal channels (i.e., the NO detector 44, the detectors for CO, $CO_2$, HC, and $H_2O$, and the reference detector 35) that were acquired prior to the vehicle 28 interrupting the beam 15 are stored by the computer 17. As the vehicle 28 exits the beam 15 so that the beam 15 is again received by the detector unit 16, the computer 17 once again begins to acquire a stream of voltage samples from each of the sensors over time. The computer 17 continues to sample voltages from each of the sensors for a period of approximately 0.1 to about 1.0 second after the vehicle 28 exits the beam 15 in the preferred embodiment. The signals from the sensors are averaged by the computer over a temporal period of approximately 1 millisecond to 20 milliseconds for each sample, with about 10 milliseconds being preferred. By thus averaging the signal a better signal-to-noise ratio is obtained.

Figure 7:
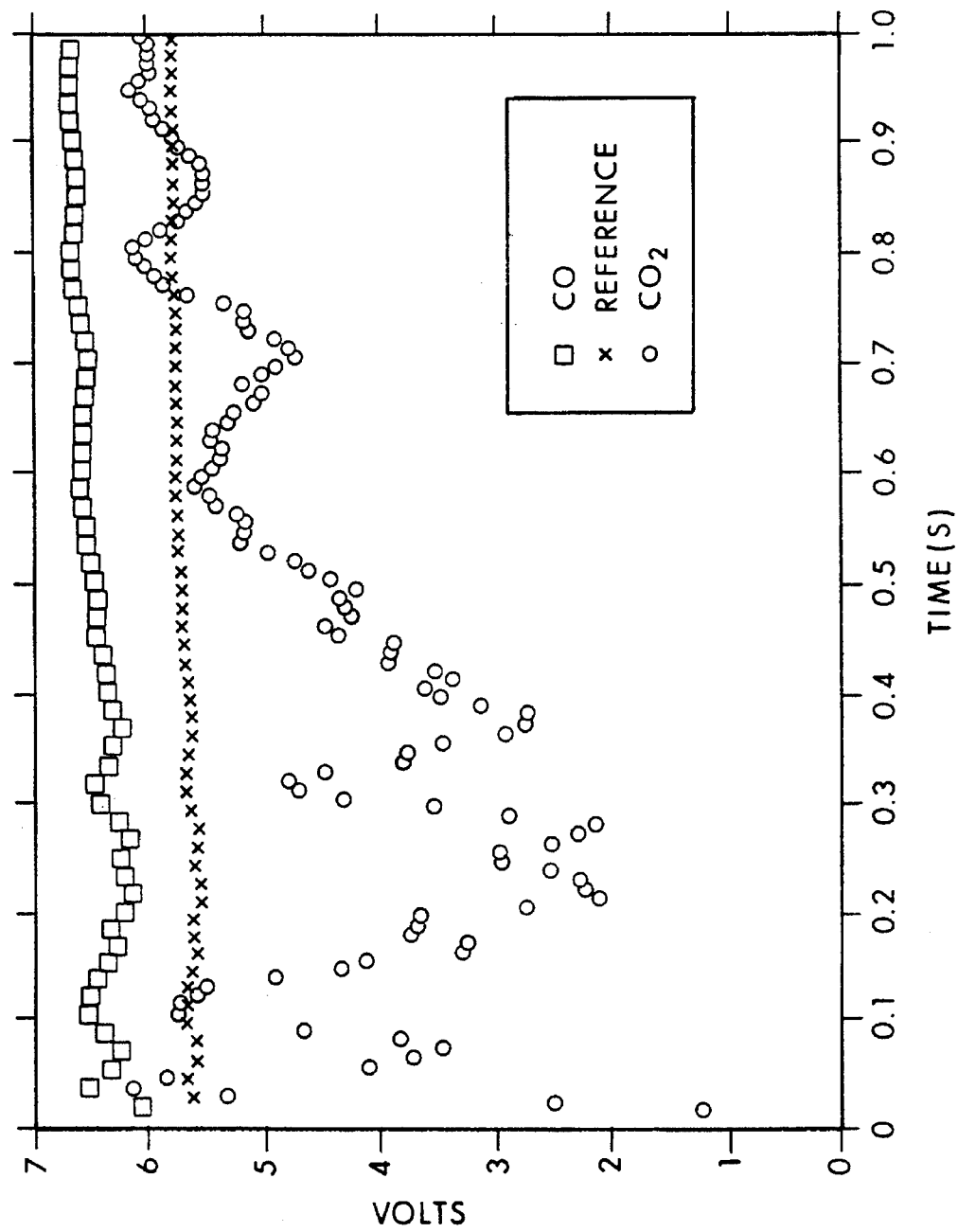
FIG. 7 is a graph showing sample voltage data as a function of time from the carbon monoxide sensor, the carbon dioxide sensor, and the reference sensor for a 1983 Oldsmobile traveling at 20 mph.
Figure 8:
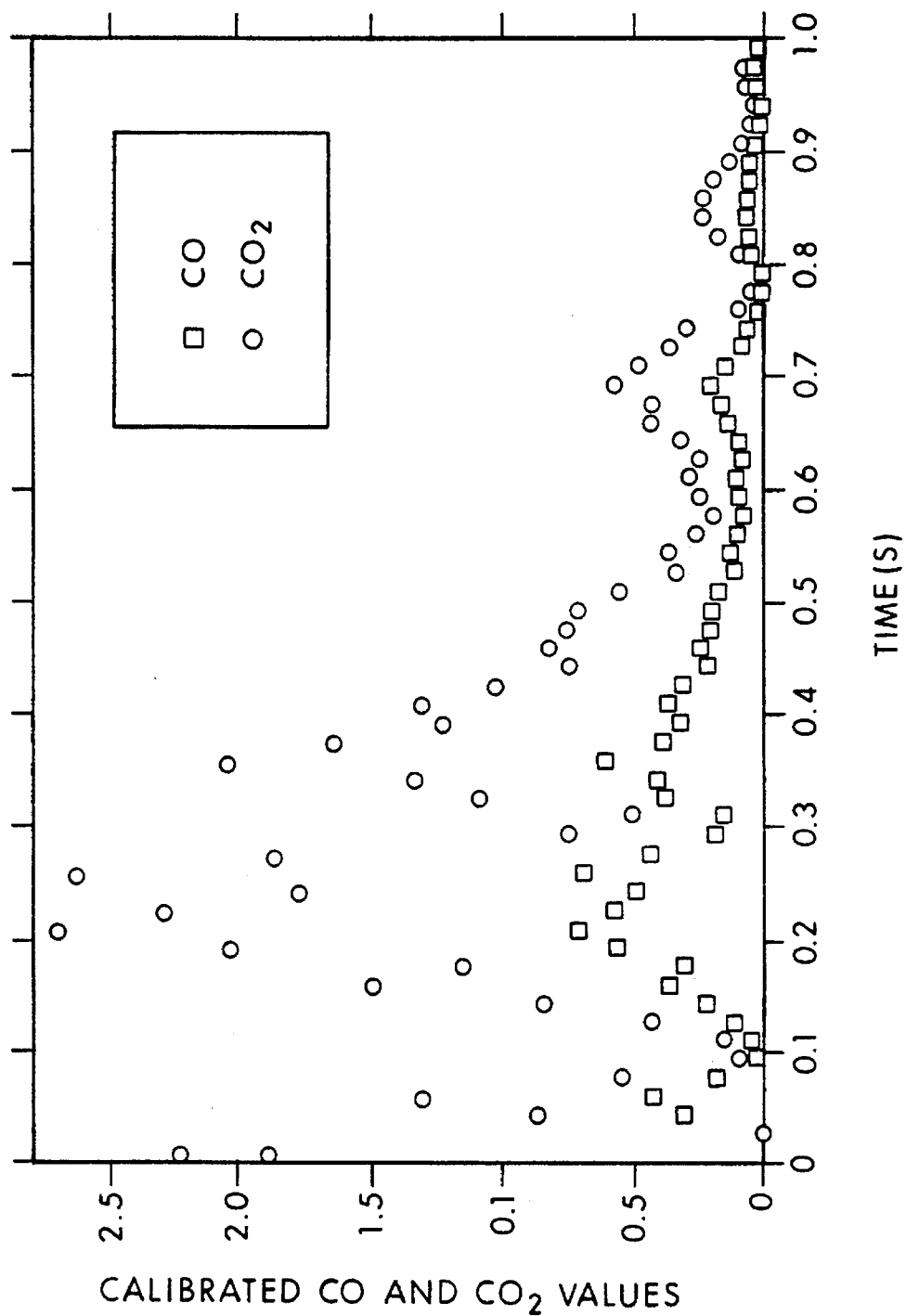
FIG. 8 is a graph showing the raw data from FIG. 7 converted to calibrated carbon monoxide and carbon dioxide values.
Figure 9:
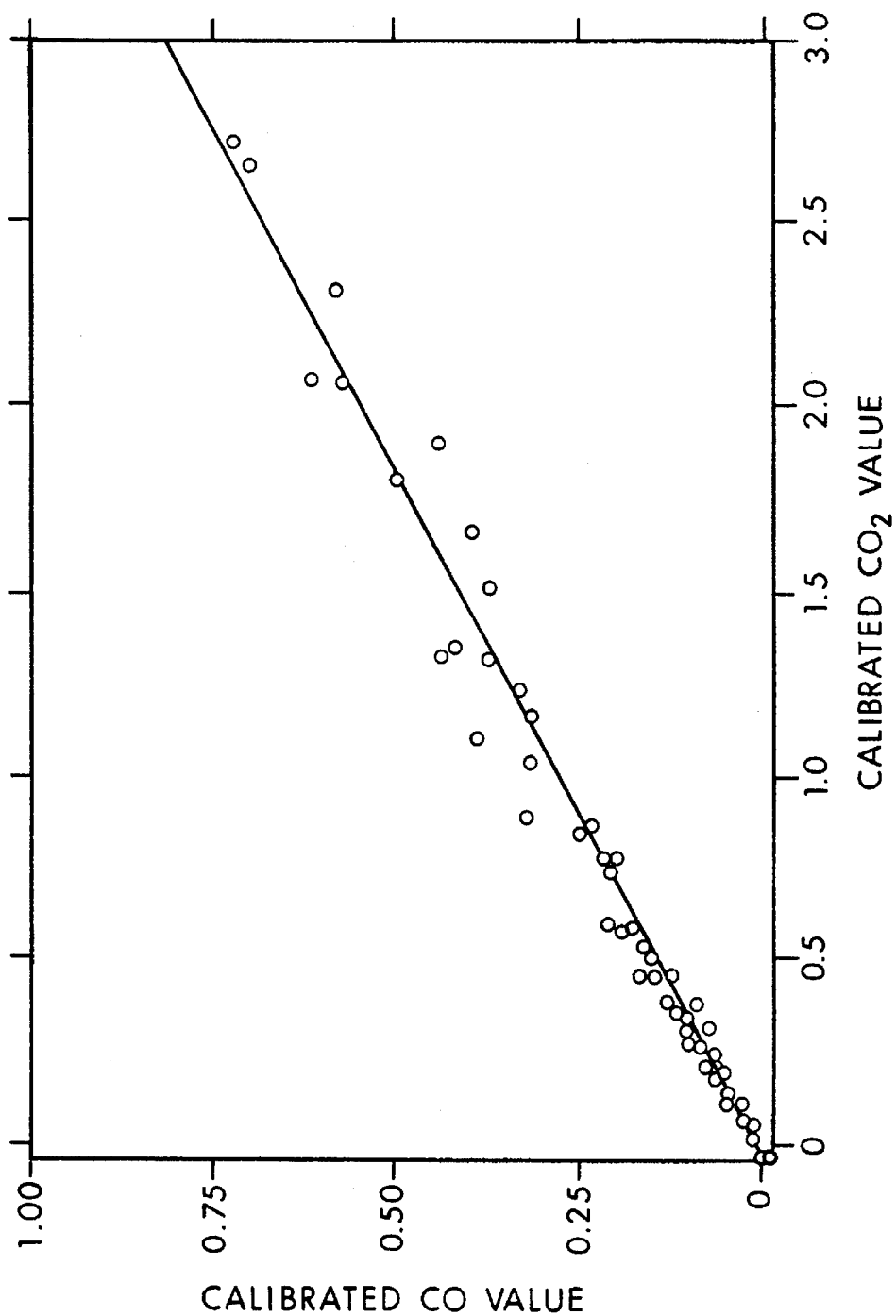
FIG. 9 is a correlation graph in which the calibrated CO and $CO_2$ values for each sample in FIG. 8 have been plotted. The slope of the line found by least-squares regression is the $CO/CO_2$ ratio, or Q.

The data analysis performed by the computer 17 can be better understood by beginning with a simplified system having only a carbon dioxide channel, a carbon monoxide channel, and a reference channel. FIG. 7 is a graph showing sample voltage data as a function of time from the carbon monoxide sensor, carbon dioxide sensor, and reference sensor for a 1983 Oldsmobile traveling at 20 mph. The raw data is then normalized by computing the ratios of the CO and $CO_2$ voltages to the reference voltages and rescaling these arbitrary units into calibrated CO and $CO_2$ values by the use of a calibration curve determined in a laboratory utilizing special flow cells with controlled mixtures of CO and $CO_2$. The calibration curve compensates for the performance characteristics of the filters and photodetectors, as well as for the relative degree of absorption at the wavelengths used in the system by carbon dioxide and carbon monoxide. FIG. 8 is a graph showing the raw data from FIG. 7 converted to calibrated carbon monoxide and carbon dioxide values. FIG. 9 is a correlation graph in which the calibrated CO and $CO_2$ values for each sample in FIG. 8 have been plotted. The computer 17 calculates the slope of this line by least-squares regression. The slope of this line, Q or $Q_{CO}$, is the $CO/CO_2$ ratio by moles.

An automobile can be considered as a device in which fuel containing carbon and hydrogen (formula $CH_n$) is burned with air whose approximate formula for this purpose is given as $0.21 O_2 + 0.79 N_2$ in a combustion chamber to derive power. The combustion products are sometimes further burned on a catalyst or in the exhaust system. However, if hydrocarbon and $NO_x$ emissions are considered to be small compared to the CO, $CO_2$, and nitrogen concentrations emanating from the tailpipe, the combustion process takes the form:

$$CH_n + m(0.21O_2 + 0.79N_2) \rightarrow \frac{n}{2}(H_2O) + \quad (1)$$

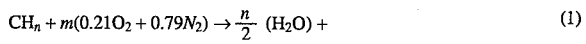
$$aCO + bCO_2 + 0.79mN_2$$

Carbon balance applied to equation (1) requires:

$$a + b = 1 \quad (2)$$

Oxygen balance applied to equation (1) requires:

$$0.42m = \frac{n}{2} + a + 2b \quad (3)$$

The definition of Q, discussed above, provides:

$$Q = \frac{a}{b} \quad (4)$$

When a and b are determined in terms of Q, one obtains:

$$a = \frac{Q}{1+Q} \quad (5)$$

and

-continued $$b = \frac{1}{1+Q} \quad (6)$$

Thus, with a knowledge of n and Q, the molar coefficients in the balanced combustion equation are readily determined. These quantities are in turn used to obtain other derived quantities.

If $CH_2$ is used for the empirical formula of the fuel, then n in equation (1) is 2, and furthermore:

$$m = \frac{1+a+2b}{0.42} \quad (7)$$

One then obtains:

$$\text{dry } CO_2 \text{ fraction} = \frac{b}{1+0.79m} \quad (8)$$

Note that any percentage errors in m caused by the assumption of n=2 will be halved for most vehicles since n is divided by 2 in this derivation. Upon substitution for b and m, one obtains:

$$CO_2 \text{fraction} = (1/(1+Q))/(1+0.79(3+2Q)/0.42(1+Q)) \quad (9)$$

After multiplying throughout by 0.42(1+Q):

$$\%CO_2 = \frac{42}{0.42+0.42Q+2.37+1.58Q} = \frac{42}{2.79+2Q} \quad (10)$$

Similarly, $$\%CO = \%CO_2 Q = \frac{42Q}{2.79+2Q} \quad (11)$$

Thus, the percentages of carbon monoxide and carbon dioxide in the exhaust can be determined from the slope of the line, Q, as shown in FIG. 9.

This type of analysis can be extended to additional channels, such as for hydrocarbons or nitrogen oxides. For example, assume that a sensor for hydrocarbons is added. A series of raw data samples is acquired by the computer 17 from the hydrocarbons sensor for a predetermined period after the vehicle passes through the beam 15, similar to that shown in FIG. 7. The raw data is normalized by the reference channel and calibrated, in the manner previously discussed, to produce calibrated HC values similar to FIG. 8. The computer then performs a least-squares regression of the calibrated HC values against the calibrated $CO_2$ values, similar to FIG. 9. The slope of the line, $Q_{HC}$, is the path-independent ratio of $HC/CO_2$ by moles. Data from the carbon monoxide channel and the carbon dioxide channel are processed by the computer as previously discussed to determine the $CO/CO_2$ ratio, or $Q_{CO}$, as before. The percentages of CO, $CO_2$, and hydrocarbons can be calculated from $Q_{CO}$ and $Q_{HC}$ as follows:

$$\%CO_2 = \frac{42}{2.79+2\,Q_{CO}-0.37\,Q_{HC}} \quad (12)$$

$$\%CO = \%CO_2 Q_{CO} \quad (13)$$

$$\%HC = \%CO_2 Q_{HC} \quad (14)$$

Similarly, if a $NO_x$ channel is added to the apparatus, the $NO_x/CO_2$ ratio or $Q_{NOx}$ is calculated in the same manner by least-squares regression from the calibrated $NO_x$ and $CO_2$ sample data. The percentage of $NO_x$ in the exhaust is determined as follows:

$$\%NO_x = \frac{42\,Q_{NOx}}{2.79+2\,Q_{CO}-0.37\,Q_{HC}} \quad (15)$$

$NO_x$ is normally such a small percentage of the exhaust gases in comparison to $CO_2$, CO, and hydrocarbons that equations (12), (13), and (14) continue to be good approximations for these gases. It should be noted that additional sensor channels can be readily included in the present system to provide similar analyses for other chemical constituents of the vehicle exhaust.

The system can be adapted to provide an indication of the exhaust system temperature using an infrared sensor with a 2.8 to 2.9 micron filter to measure the amount of water present in the exhaust. Cold engines tend to generate substantially more pollutants than warm engines, and also to produce water droplets rather than vapor as would an engine operating above 100° C. A one to one molar ratio of water vapor to CO and $CO_2$ would indicate a warm engine, while a smaller ratio would indicate a cold engine. By measuring the amount of water vapor as compared to CO and $CO_2$, it can be determined whether an engine was running with high emissions because it was cold or because the vehicle emission systems were malfunctioning.

In addition, this water sensor can be used to measure the amount of liquid-phase water in the form of droplets or steam present in the exhaust to flag possibly erroneous readings from the hydrocarbons channel. Water droplets also show strong absorption at 3.3 and 3.4 microns, which is the wavelength used by the hydrocarbons channel. Thus, water droplets from a cold engine can be erroneously interpreted by the hydrocarbons sensor as a very large hydrocarbons emission. The water channel has the advantage of accurately measuring water without hydrocarbons interference. A reading from the water sensor showing large amounts of water droplets can be used as a flag to indicate that the corresponding reading from the hydrocarbons sensor is probably inaccurate and should be ignored.

Solid particulate matter is becoming more and more a matter of concern. It is abundantly clear that the system of the present invention may also be easily adapted to measure the opacity of the exhaust of a vehicle, and thereby provide an indication of the nongaseous particulate matter being generated by the vehicle engine.

Figure 6:
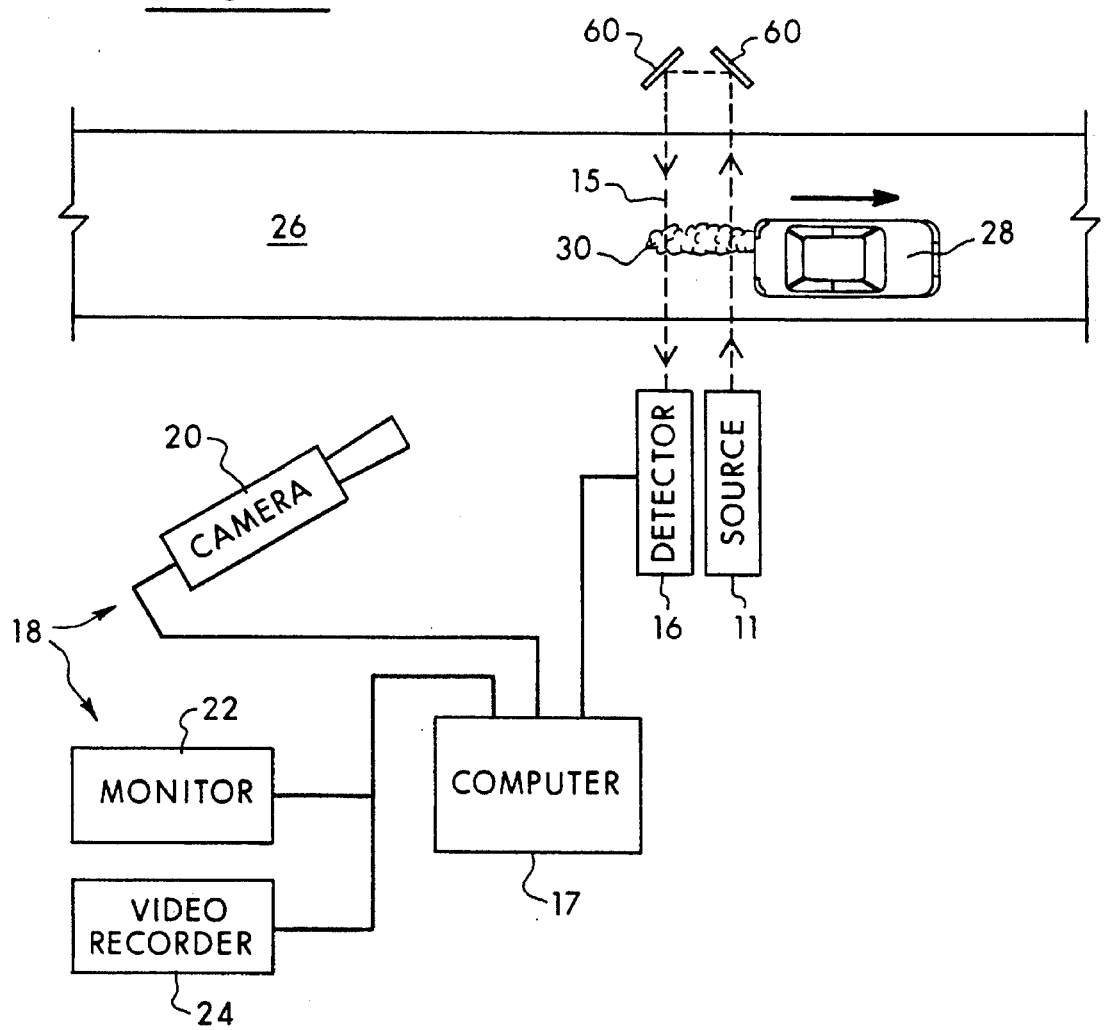
FIG. 6 is a schematic diagram of an alternative embodiment of the system in which the source and detector are located on the same side of the roadway. A reflector 60 located on the opposite side of the roadway is used to reflect the beam from the source 11 to the detector unit 16 with two passes through the vehicle exhaust.

Currently contemplated state of the art modifications include the incorporation of both the infrared and ultraviolet radiation sources and the detector system in a single unit or in side by side units on the same side of the roadway 26 as shown in FIG. 6. In such an instance the source 11 sends the beam 15 out to one or more reflectors 60 that return the beam 15 to the detector unit 16 for processing as detailed above. This arrangement simplifies operation of the system (after initial setup) by having both the detector 16 and source 11 adjacent to one another on one side of the roadway. In addition, this arrangement increases the absorption signal by providing two passes of the beam 15 through the vehicle exhaust plume 30 on-road.

Figure 10:
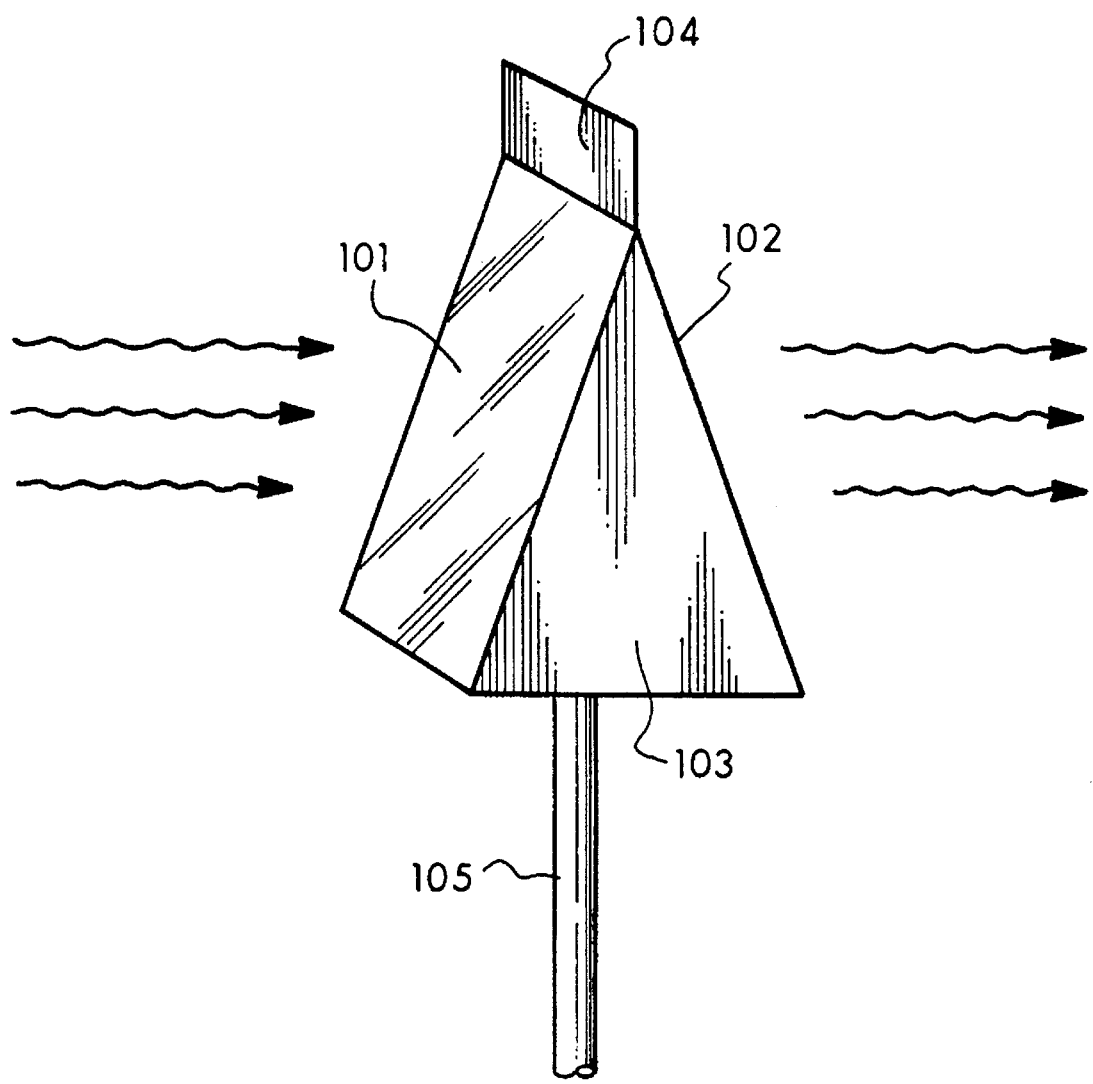
FIG. 10 is a perspective view of the wedge-shaped gas cell used to calibrate the system.

FIG. 10 shows the wedge-shaped gas cell used for calibration of the system. The cell has two transparent windows 101 and 102 that permit a beam of light to pass through a wedge-shaped cavity within the cell. The remaining walls 103 of the cell are typically made of an opaque material, such as aluminum. The cavity within the cell between the transparent windows 101 and 102 is filled with a known mixture of all of the gases monitored any given configuration by the system. For example, a typical gas mixture is 47% CO, 47% $CO_2$, and 6% propane for a system having CO, $CO_2$, and hydrocarbons channels. A handle 105 attached to the bottom of the cell is used to gradually slide the cell across the path of the beam 15 in the detector unit 16. The triangular or wedge-shaped cross-section of the cell provides variation in length of the optical path for the beam 15 through the cell as the cell is moved across the beam 15. An opaque blade 104 extends forward along the leading edge of the cell. The blade 104 is the first portion of the calibration cell to enter the beam 15 and provides the same zero reference to begin the calibration process as is provided by a passing automobile. As the cell is inserted further into the beam 15, absorption of the beam by the gases within the cell progressively increases as the optical path through the cell correspondingly lengthens. The computer 17 continually samples the output of the sensors for each channel as the calibration cell is inserted. Since the ratio of the gas mixture within the cell remains constant, the samples from the CO and CO$_2$ channels during calibration should trace out a relatively straight line when plotted in the form of a correlation graph such as FIG. 9. In particular, the sample points should begin near the lower left corner of the graph when the optical path through the cell is at a minimum, and then proceed upward and to the right along a line as the length of the optical path increases. The slope of this line, $Q_{CO}$, is then compared against the known ratio of concentrations CO and CO$_2$ within the cell for the purpose of determining an appropriate calibration factor for carbon monoxide. A similar analysis is performed for the ratio of hydrocarbons to CO$_2$ if the unit has a hydrocarbons channel, and for the ratio of NO to CO$_2$ if the unit has a NO channel.

In one possible alternative embodiment, the calibration cell has a series of steps along its length to provide regions of differing cross-sectional widths. For example, a stepped triangular cross-section can be used.

Figure 11:
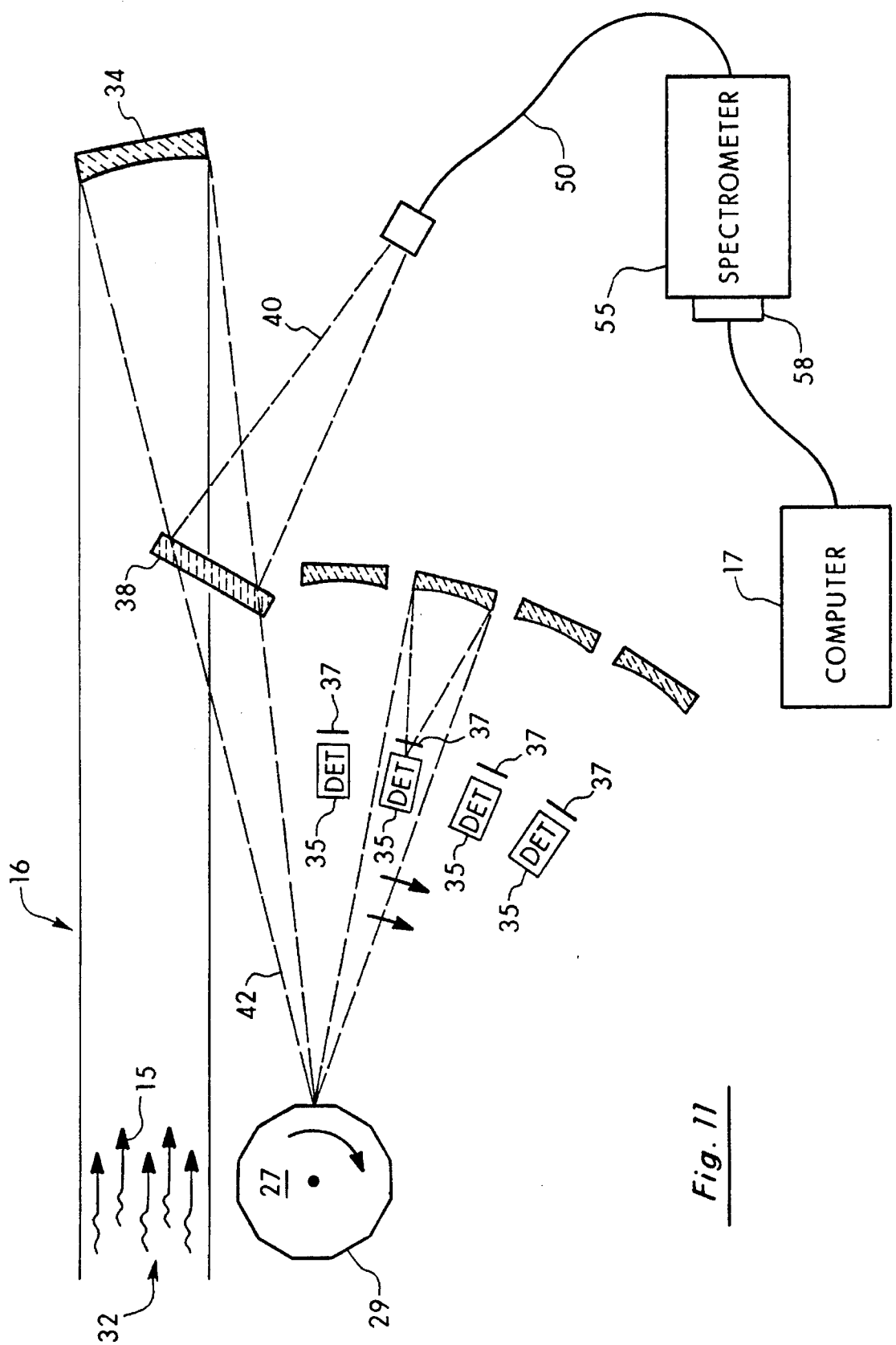
FIG. 11 is a schematic diagram of an alternative embodiment of the detector unit 16 using an ultraviolet beam and a spectrometer to measure the concentration of nitric oxide (NO) in the vehicle exhaust.

FIG. 11 is a schematic block diagram of an alternative embodiment of the detector 16 in which the filter 52 and photomultiplier tube 44 have been replaced with a spectrometer 55 to measure the concentration of nitric oxide (NO). The remainder of the system is largely unchanged. As before, the light source 11 transmitts a collimated beam 15 combining both infrared and ultraviolet light through the exhaust plume 30 behind the vehicle 28. The detector 16 includes a beamsplitter 38 to separate the infrared beam 42 from the ultraviolet beam 40. The ultraviolet beam 40 is then diffracted by means of a prism or diffraction grating within the spectrometer 55. The resulting spectrum is directed onto an array of photodiodes 58, so that each photodiode generates a voltage proportional to the intensity of the light within a corresponding narrow segment of the spectrum.

Figure 12:
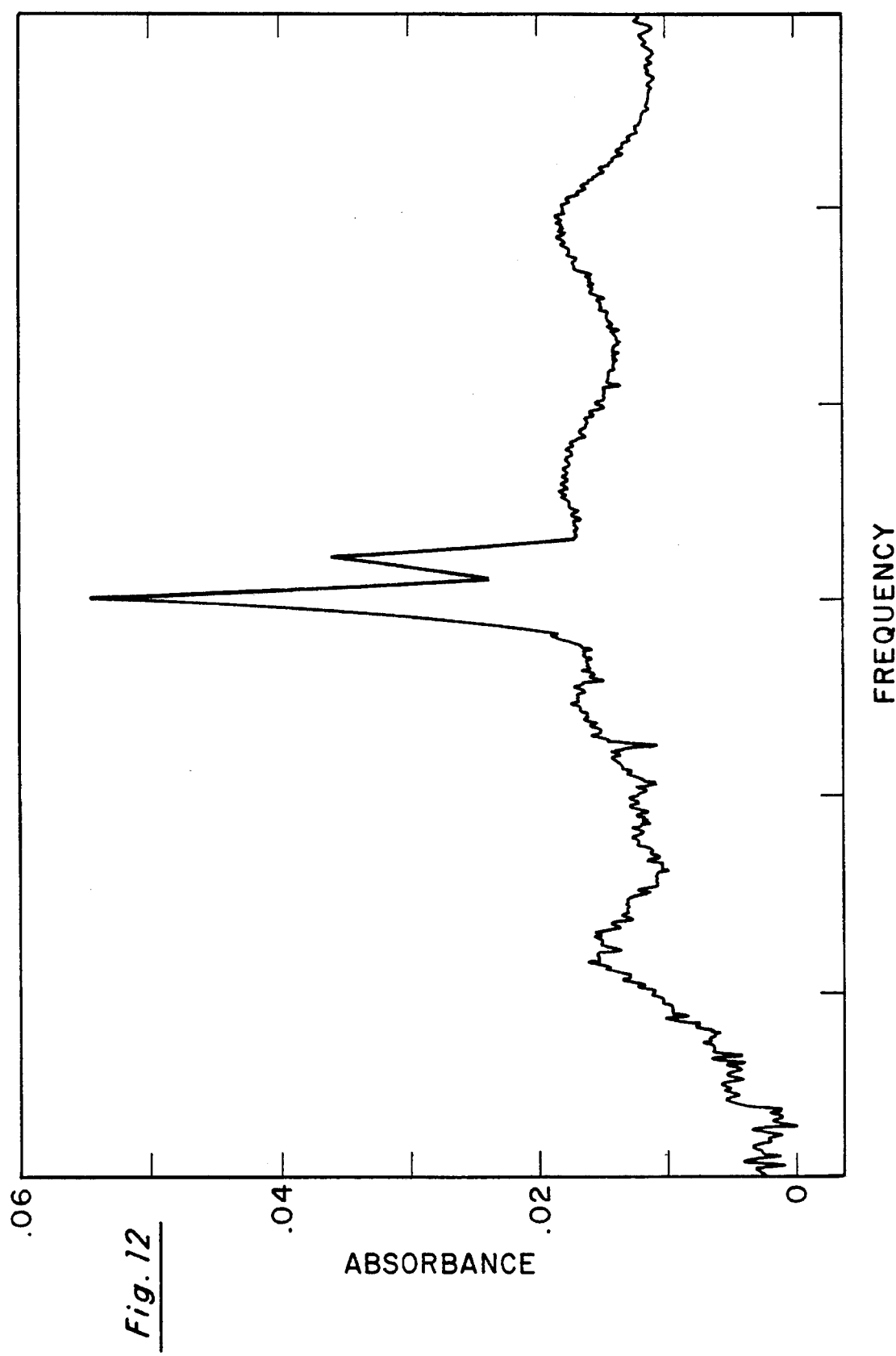
FIG. 12 is a chart showing absorbance of the ultraviolet beam as a function of frequency measured by the spectrometer.

FIG. 12 is a graph of a typical absorbance spectrum produced by the spectrometer 55 from the ultraviolet beam passing through the exhaust plume of a moving vehicle. This graph clearly shows an absorbance peak at a wavelength of approximately 227 nm. Therefore, the output signals from the corresponding elements in the photodiode array 58 can be employed as an indication of the concentration of NO in the exhaust plume. The output signals from other photodiodes in the array outside of the peak can be used to establish a reference signal indicating total absorption of the ultraviolet beam by the exhaust. The output signals from the photodiode array 58 are converted into digital form and periodically sampled by the computer 17. Alternatively, the photodiode array 58 could be replaced with a rapid slit scanner and a photomultiplier tube. As previously described, the computer 17 typically samples the output signal from each of the infrared sensors and the spectrometer for a predetermined period following resumption of the beam reception by the detector after a moving vehicle interrupts the beam.

The NO/CO$_2$ ratio or $Q_{NO}$ is calculated by least-squares regression from calibrated NO and CO$_2$ sample data. The percentage of NO in the exhaust is determined as follows, similar to equation (15):

$$\%NO = \frac{42\,Q_{NO}}{2.79 + 2\,Q_{CO} - 0.37\,Q_{HC}} \quad (16)$$

NO is normally such a small percentage of the exhaust gases in comparison to CO$_2$, CO, and hydrocarbons that equations (12), (13), and (14) continue to be good approximations for these gases.

As previously stated, equations (1) through (16) are based on assumptions that hydrocarbon and NO$_x$ (or NO) emissions are very small compared to the CO, CO$_2$, and nitrogen concentrations emanating from the vehicle tailpipe. Alternative derivations of these equations can be used. For example, the following combustion reaction includes NO and unburned hydrocarbon emissions in the vehicle exhaust:

$$CH_n + m(0.21O_2 + 0.79N_2) \rightarrow \frac{n}{2} H_2O + \quad (17)$$

$$aCO + bCO_2 + cCH_2 + dNO + \left(0.79m - \frac{d}{2}\right)N_2$$

Unburned hydrocarbons are assumed to be emitted as a mixture of hydrocarbons having an average empirical hydrogen-to-carbon ratio of 2:1, which can be approximated as CH$_2$. Again, n=2 for fuel having an empirical formula of CH$_2$. A carbon balance applied to equation (17) requires:

$$a+b+c=1 \quad (18)$$

An oxygen balance applied to equation (17) requires:

$$0.42m = a + 2b + 1 + d \quad (19)$$

The following Q ratios can then be derived:

$$Q = Q_{CO} = \frac{a}{b} = \frac{CO}{CO_2} \quad (20)$$

$$Q_{HC} = \frac{c}{b} = \frac{HC}{CO_2} \quad (21)$$

$$Q_{NO} = \frac{d}{b} = \frac{NO}{CO_2} \quad (22)$$

One then obtains the following dry percentage calculations:

$$\%CO_2 = \frac{42}{2.79 + 2Q + 0.42Q_{HC} + Q_{NO}} \quad (23)$$

and $$\%NO = \frac{42Q_{NO}}{2.79 + 2Q + 0.42Q_{HC} + Q_{NO}} \quad (24)$$

Equations (17) through (24) will typically produce results that are essentially the same as equations (1) through (16) for most vehicles.

A quartz optical fiber 50 can be employed to transport the ultraviolet beam 40 from the beamsplitter 38 to the port of the spectrometer 55, as shown in FIG. 11. This simplifies packaging of the spectrometer within a common housing with the remainder of the detector components, and also provides greater flexibility in adjusting optical alignment.

The spectrometer has both advantages and disadvantages. The primary disadvantages are substantially increased cost and complexity of the system. The primary advantage is the ability of the spectrometer to achieve higher resolution than the filter/photomultiplier arrangement described above. The first embodiment shown in FIG. 3 works well in distinguishing vehicles that emit gross amounts of pollution (>3,000 ppm NO) from relatively clean cars (approximately 1,000 ppm NO). However, the second embodiment significantly increases the signal-to-noise ratio for NO detection by about an order of magnitude. Another advantage is that the spectral data produced by the spectrometer can be used to unequivocally identify a specific compound (e.g., nitric oxide) based on a unique combination of known peaks associated with the compound. This helps to identify interferences between compounds and can also be used to identify unknown compounds that may be present in vehicle exhaust, based on the shape and location of absorption peaks in the UV spectrum. The system can also be readily adapted to detect compounds other than NO having absorption peaks in the UV region, such as benzene, toluene, xylene, and $NO_2$.

As can be seen from the above, the present invention provides a unique system for the remote measuring and monitoring of emissions from moving motor vehicles. In particular, the present invention provides for a device that will simultaneously measure CO, $CO_2$, HC, NO, and $H_2O$ depending on a desired measurement. This particular invention allows a remote sensing and measuring system so that vehicles do not have to be stopped and can be spot-checked at any given time. Moreover, this particular system permits the visual display as well as permanent recording of such display of the actual vehicle, including license plate identification, which is displayed in conjunction with the exhaust measurements. Such a system could be utilized to enforce emission standards under real-use conditions, or to simply obtain real-time measurements so as to permit vehicle owners to be made aware of necessary corrections of vehicle emissions. The capability of measuring nitrogen oxides and hydrocarbons levels is particularly useful, since there is presently no existing system available that allows such measurements, and such measurements are crucial to the whole emission picture of any given vehicle. The unique capability of measuring NO and hydrocarbons in conjunction with CO and $CO_2$, as well as identifying by license place number the specific vehicle responsible for such emissions for both immediate and future use is exceptionally beneficial, both from an emissions enforcement aspect as well as from environmental aspects to permit the actual owner and operator of the vehicle to be aware of real-time use emissions of the vehicle.

FIGS. 13 through 17 relate to an alternative embodiment of the present invention in which an infrared detector is used to remotely determine whether the vehicle engine is hot or cold by measuring infrared radiation reflected by the roadway beneath the vehicle. As previously discussed, a cold vehicle may temporarily produce elevated emissions levels that are not truly indicative of the vehicle's performance under normal operating conditions. If the present system is used to screen large numbers of passing vehicles to determine which vehicles have emissions levels exceeding predetermined standards, this can lead to cold vehicles being falsely identified as high polluters. Therefore, the system should only identify hot vehicles having excessive emissions.

It is well known that the intensity of infrared radiation emitted by a body increases with temperature. This means that a hot engine will emit substantially more infrared radiation than a cold engine. However, it is difficult to remotely measure infrared radiation from an engine under normal driving conditions because the hood and exterior panels of the vehicle substantially block any direct view of the engine from the top, front, or sides of vehicle. The present invention relies on the discovery that most conventional roadways reflect infrared radiation directed downward by the engine and exhaust components of vehicles.

Figure 13:
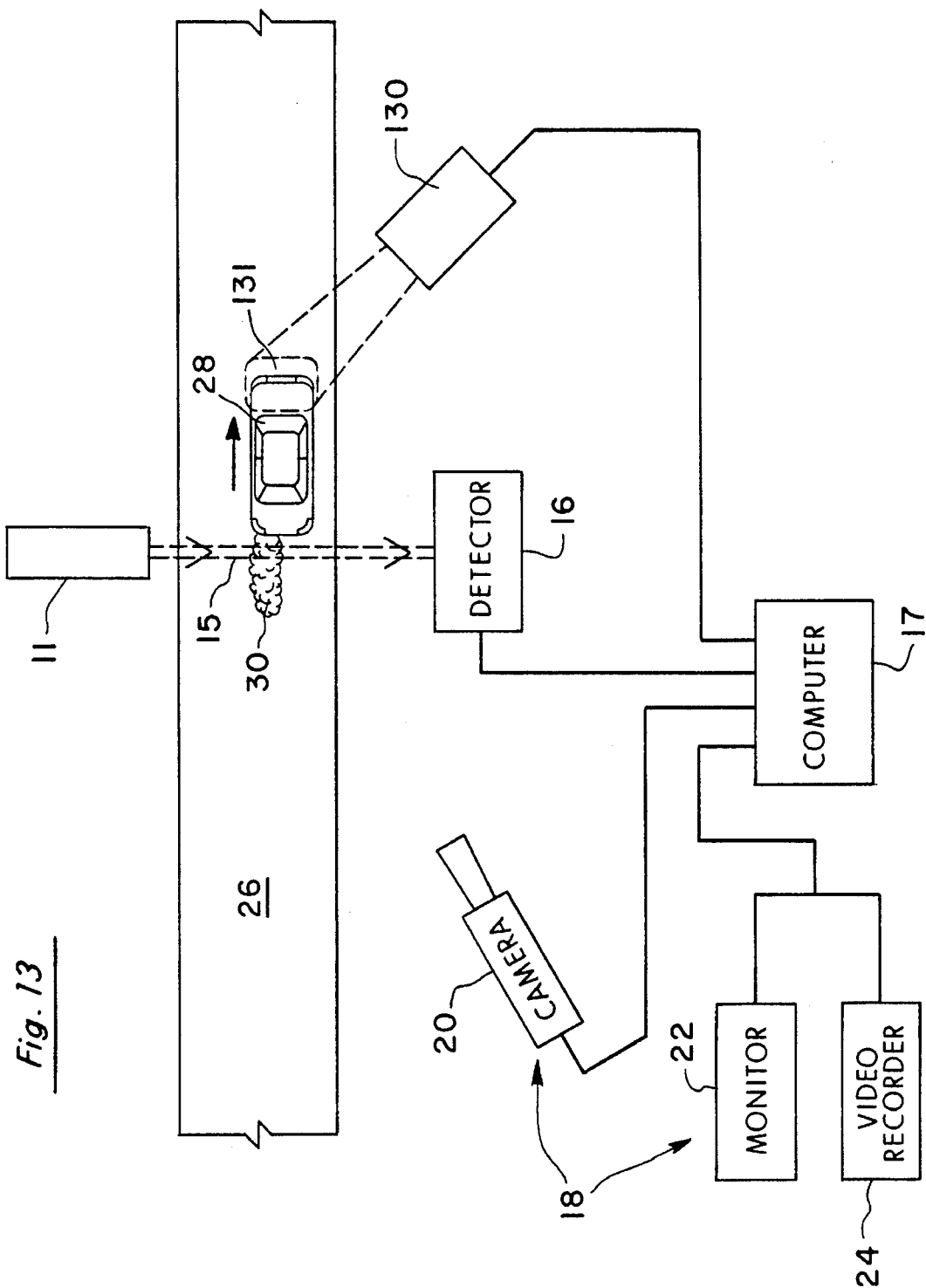
FIG. 13 is a schematic diagram similar to FIG. 1 showing an alternative embodiment of the present invention in which an infrared detector is used to measure the intensity of infrared radiation reflected by the roadway to determine whether the vehicle's engine is hot or cold.
Figure 15:
FIG. 15 is a typical infrared image of a car with a cold engine.
Figure 16:
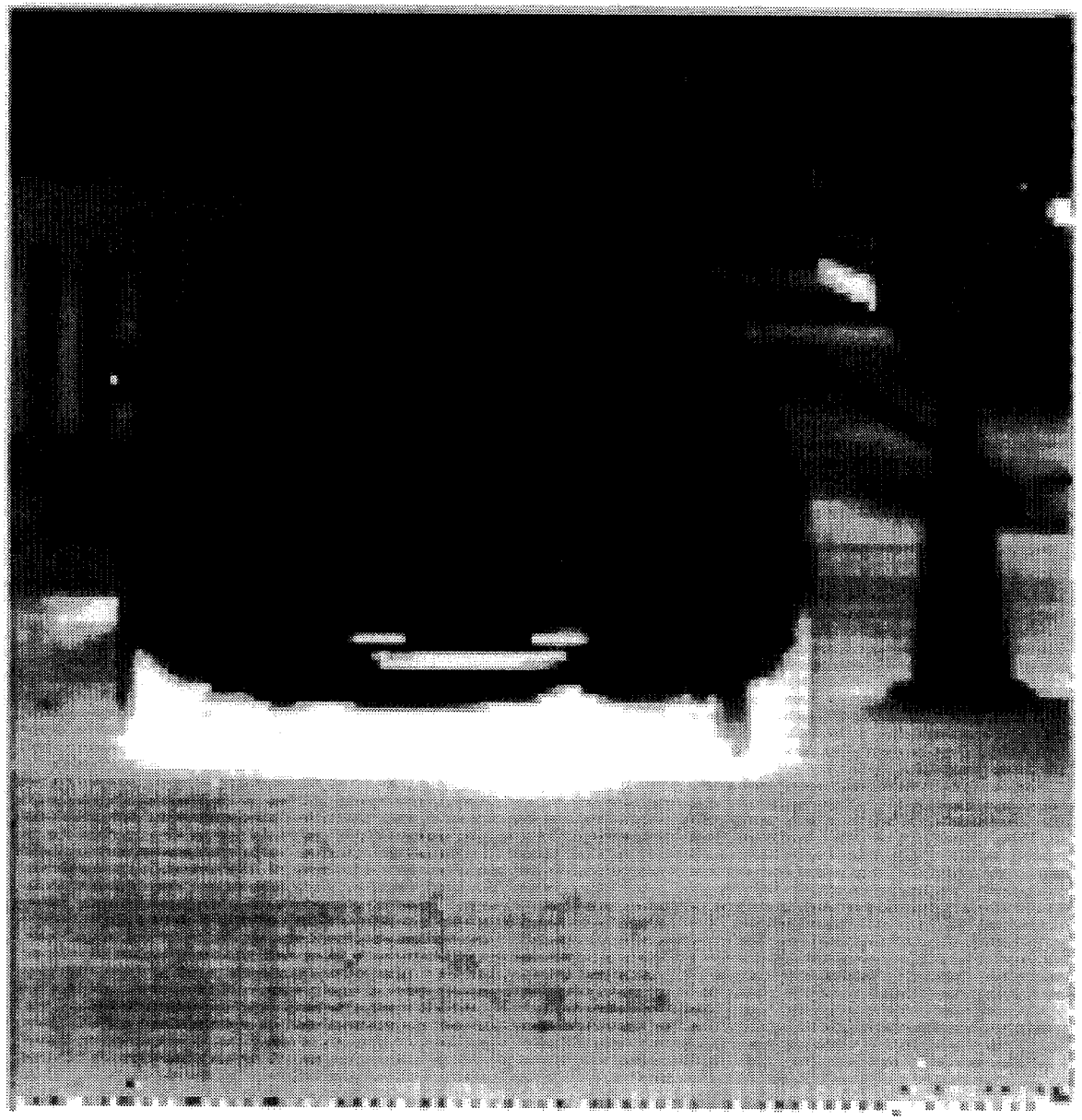
FIG. 16 is a typical infrared image of a car having an engine at an intermediate temperature.
Figure 17:
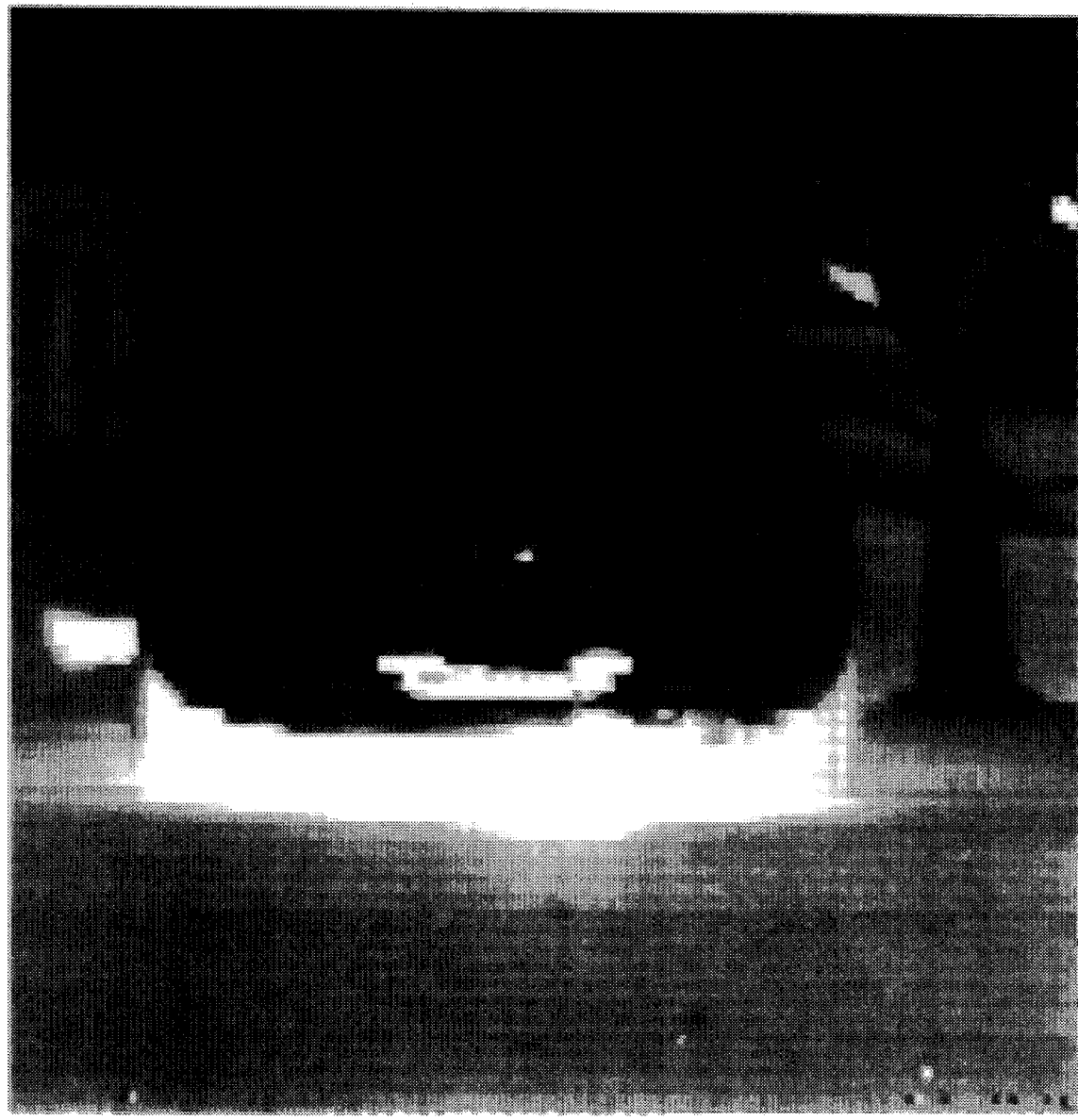
FIG. 17 is a typical infrared image of a car with a hot engine.

FIG. 13 is a schematic diagram of this alternative embodiment. An infrared detector 130 is positioned by the side of the roadway to measure infrared radiation emitted by each vehicle passing through the beam 15. The infrared detector 130 can either be a photodetector that produces an analog electrical signal proportional to the overall intensity of infrared radiation within its field of view 131, or an infrared camera that produces a thermographic image. For example, FIGS. 15 through 17 are a series of thermographic images showing infrared emissions reflected by the roadway beneath a typical vehicle as its engine and exhaust components gradually warm from a cold state (FIG. 15), through an intermediate phase (FIG. 16), to a hot state (FIG. 17) corresponding to the normal operating temperature of the engine. In either case, data from the infrared detector 130 is fed to the computer processor 17 to determine the intensity of infrared radiation within the field of view 131. In the case of an infrared camera, the processor 17 scans the pixels in the image to determine the region of maximum infrared intensity. If the image contains at least one region of minimal size having an infrared intensity exceeding a predetermined limit, the processor determines that the vehicle is hot. Otherwise the processor determines that the vehicle is cold. A thermographic image also provides increased flexibility by allowing use of imaging processing algorithms to filter out extraneous glare and to identify the relevant regions of the image for analysis. However, the cost of a thermographic camera may be prohibitive for many applications.

Figure 14:
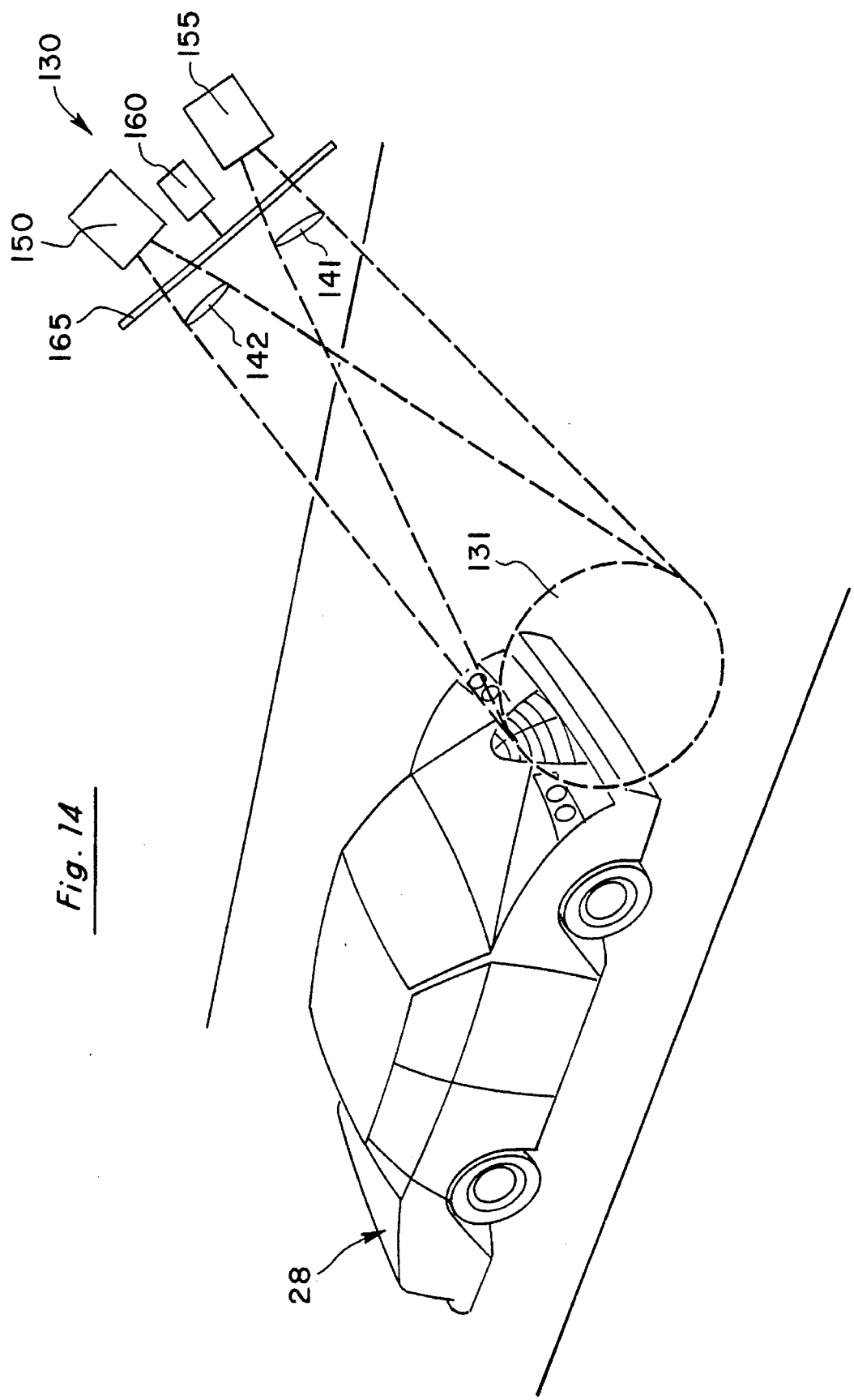
FIG. 14 is a schematic diagram of the alternative embodiment depicted in FIG. 13 providing additional detail of the infrared detector.

FIG. 14 is a schematic diagram providing additional details of an infrared detector 130 that is substantially less complicated and expensive. The detector 130 includes two photodetectors 150 and 155 that measure the intensity of infrared radiation and visible light, respectively. The visible light photodetector 155 will detect sunlight, reflections, and glare. Two lenses 141 and 142 focus light from predefined fields of view 131 onto the photodetectors. Ideally, the fields of view substantially overlap as shown in FIG. 14. The field of view 131 includes the front portion or side portion of the vehicle adjacent to its engine and a portion of the roadway beneath the vehicle, so that infrared radiation emitted by the engine and exhaust components of the vehicle is reflected by the roadway within the field of view 131 of the infrared detector 130. For example, the field of view can be a roughly circular region having a diameter of about six feet at the roadway.

An optical chopper 165, such as a rotating disk having a radial arrangement of openings driven by a motor 160 alternately blocks and unblocks the field of view for the infrared photodetector 150 and the visible light photodetector 155. This causes the infrared photodetector 150 to generate an output signal that alternates between a reference value corresponding to darkness and a value corresponding to the intensity of infrared radiation within its field of view. Similarly, the output signal from the visible light photodetector 155 alternates between a reference value corresponding to darkness and a value corresponding to the intensity of visible light within its field of view. These reference values provide a baseline for calibration.

The output signals from the photodetectors 150, 155 are periodically sampled by the computer processor 17. The processor determines the vehicle is hot if the infrared signal exceeds a first predetermined limit and the visible light signal does not exceed a second predetermined limit. If both the infrared and visible light signals are low, the vehicle is probably cold. If the visible light signal exceeds the second limit, the detector 130 is being excessively affected by sunlight, reflections, or glare and vehicle's temperature state cannot be determined with certainty.

The limits for the visible light detector and the infrared detector must be determined for each installation due to the wide variation in conditions that can be expected based on geographical location, weather conditions, orientation, time of day, type of road surface, etc. The maximum limit for the visible light detector can be set a fixed ratio (e.g., 150%) of average ambient visible light within the field of view of the visible light detector 155. The limit for the infrared detector can be determined by an initial statistical analysis of a large number of passing vehicles (e.g., the first few hundred vehicles) based on an assumption that most of the vehicles are warmed up.

The computer processor 17 determines the emissions levels for each vehicle as previously discussed, and whether the vehicle is hot or cold based on the readings from the infrared detector 150 and visible light detector 155. In the preferred embodiment, the processor 17 sets a flag or indicator for each vehicle indicating whether the vehicle is cold. The vehicle owner may be notified if the vehicle's emissions levels exceed predetermined limits and the vehicle is hot. Otherwise, no further action is taken with respect to the vehicle. As previously discussed, a video camera and video tape recorder can be employed to record images of the license plate and emissions readings for passing vehicles—particularly those hot vehicles having excessive emissions levels. This system can also be employed to record data from the infrared and visible light detectors (or thermographic images) to substantiate the thermal state of the vehicle.

The preceding discussion has assumed that the thermal condition of the vehicle is to be ascertained in conjunction with a system for remotely measuring vehicle exhaust emissions. However, it should be expressly understood that the present invention can be employed in association with other types of systems for monitoring vehicle emissions. For example, many states have adopted mandatory vehicle emissions testing programs using centralized testing facilities. In some states, vehicle emissions are monitored as the vehicle runs on a stationary dynamometer. Other states have adopted testing programs that measure engine emissions while the vehicle is parked. In either case, the vehicle engine and exhaust system must be hot for the test to produce accurate results. The present system could be applied to such centralized testing programs to ensure that each vehicle entering the testing facility is hot before the operator expends the time and effort necessary to drive the vehicle into position in a testing bay and connect the necessary testing equipment to the vehicle. For example, the present system could be located near the entrance to the testing facility. If a vehicle entering the facility is determined to be cold, its owner would be asked to continue driving the vehicle for few more minutes before entering the testing facility.

While the invention has been particularly shown, described, and illustrated in detail with reference to preferred embodiments and modifications thereof, it should be understood by those skilled in the art that the foregoing and other modifications are exemplary only, and that equivalent changes in form and detail can be made therein without departing from the true spirit and scope of the invention as claimed, except as precluded by the prior art.

We claim:

1. A system for remotely identifying the thermal state of motor vehicles on a roadway, each vehicle having an engine and exhaust system components (the "components") which may initially be cold after said engine is first started (the "cold state") and which become hot after a period of operation (the "hot state"); wherein said components in said hot state emit substantially more infrared radiation than components in said cold state, with at least a portion of said infrared radiation being directed toward said roadway; said system comprising:

an infrared detector for detecting infrared radiation within a field of view including at least a portion of said roadway beneath said vehicle; and a processor for determining whether said vehicle is in said hot state by measuring the intensity of infrared radiation detected by said infrared detector while said vehicle is within said field of view.

2. The system of claim 1 further comprising a visible light detector for detecting the intensity of visible light within a field of view that at least partially overlaps said field of view of said infrared detector, and wherein said processor determines that said vehicle is in said hot state if the intensity of infrared radiation detected by said infrared detector exceeds a first predetermined limit and the intensity of visible light detected by said visible light detector does not exceed a second predetermined limit.

3. The system of claim 2 wherein said system is initially used to measure intensities of said infrared radiation and said visible light at a fixed location for a number of passing vehicles, and wherein said processor then calculates said first limit for infrared radiation and said second limit for visible radiation from said measured intensities for said passing vehicles by assuming that a predetermined statistical percentage of said passing vehicles are in said hot state.

4. The system of claim 1 further comprising optical chopper means for alternately blocking and unblocking said field of view of said infrared detector so that said infrared detector produces a signal that alternates between a reference value corresponding to darkness and a value corresponding to the intensity of infrared radiation from said field of view.

5. The system of claim 1 wherein said infrared detector comprises an infrared camera producing a thermographic image of said field of view, and wherein said processor means determines that said vehicle is in said hot state if said thermographic image contains at least one region having an infrared intensity exceeding a predetermined limit.

6. The system of claim 1 wherein said vehicle includes a front portion housing said engine, and wherein said field of view of said infrared detector includes a portion of said roadway adjacent to said front portion of said vehicle.

7. The system of claim 1 wherein said vehicle includes a side portion, and wherein said field of view of said infrared detector includes a portion of said roadway adjacent to said side portion of said vehicle.

8. A gas analysis system for remotely identifying moving motor vehicles on a roadway having concentrations of exhaust gases above predetermined limits, each of said vehicles having an engine and exhaust system components (the "components") that may initially be cold after said engine is first started (the "cold state") and that become hot after a period of operation (the "hot state"); wherein said components in said hot state emit substantially more infrared radiation than components in said cold state, with at least a portion of said infrared radiation being directed toward said roadway; said system comprising:

a source for producing and transmitting a beam of radiation through at least a portion of the exhaust of a motor vehicle; and a plurality of sensors for receiving said beam, each sensor generating a signal indicative of the absorption of said beam in a wavelength band indicative of a corresponding one of said exhaust gases;

an infrared detector for detecting infrared radiation within a field of view including at least a portion of said roadway beneath said vehicle; and a processor responsive to said sensors for computing the concentrations of said exhaust gases in the path of said beam through said exhaust, and for determining whether said vehicle is in said hot state by measuring the intensity of infrared radiation detected by said infrared detector while said vehicle is within said field of view, said processor identifying each vehicle for which said concentrations of said exhaust gases exceed said predetermined limits if said vehicle is determined to be in said hot state.

9. The system of claim 8 further comprising a visible light detector for detecting the intensity of visible light within a field of view that at least partially overlaps said field of view of said infrared detector, and wherein said processor determines that said vehicle is in said hot state if the intensity of infrared radiation detected by said infrared detector exceeds a first predetermined limit and the intensity of visible light detected by said visible light detector does not exceed a second predetermined limit.

10. The system of claim 9 wherein said system is initially used to measure intensities of said infrared radiation and said visible light at a fixed location for a number of passing vehicles, and wherein said processor then calculates said first limit for infrared radiation and said second limit for visible radiation from said measured intensities for said passing vehicles by assuming that a predetermined statistical percentage of said passing vehicles are in said hot state.

11. The system of claim 8 further comprising optical chopper means for alternately blocking and unblocking said field of view of said infrared detector so that said infrared detector produces a signal that alternates between a reference value corresponding to darkness and a value corresponding to the intensity of infrared radiation from said field of view.

12. The system of claim 8 wherein said infrared detector comprises an infrared camera producing a thermographic image of said field of view, and wherein said processor means determines that said vehicle is in said hot state if said thermographic image contains at least one region having an infrared intensity exceeding a predetermined limit.

13. The system of claim 8 wherein said vehicle includes a front portion housing said engine, and wherein said field of view of said infrared detector includes a portion of said roadway adjacent to said front portion of said vehicle.

14. The system of claim 8 wherein said vehicle includes a side portion, and wherein said field of view of said infrared detector includes a portion of said roadway adjacent to said side portion of said vehicle.

15. The system of claim 8 further comprising a camera aligned to record an image of each vehicle identified by said processor, including any vehicle identification material displayed on said vehicle.

16. The system of claim 15 wherein said camera comprises a video camera, and wherein said system further comprises video recording means for storing said vehicle image together with data regarding said concentrations of said exhaust gases measured for said vehicle.

17. A gas analysis system for remotely identifying moving motor vehicles on a roadway having concentrations of exhaust gases above predetermined limits, each of said vehicles having an engine and exhaust system components ("components") that may initially be cold after said engine is first started (the "cold state") and that become hot after a period of operation (the "hot state"); wherein said components in said hot state emit substantially more infrared radiation than components in said cold state, with at least a portion of said infrared radiation being directed toward said roadway; said system comprising:

a source for producing and transmitting a beam of radiation through at least a portion of the exhaust of a motor vehicle;

a plurality of sensors for receiving said beam, each sensor generating a signal indicative of the absorption of said beam in a wavelength band indicative of a corresponding one of said exhaust gases;

an infrared detector for detecting infrared radiation within a field of view including at least a portion of said roadway beneath said vehicle;

a visible light detector for detecting visible light within a field of view that at least partially overlaps said field of view of said infrared detector; and a processor responsive to said signals from said sensors for computing the concentrations of said exhaust gases in the path of said beam through said exhaust, and for determining whether said vehicle is in said hot state by measuring whether the intensity of infrared radiation detected by said infrared detector exceeds a first predetermined limit and the intensity of visible light detected by said visible light detector does not exceed a second predetermined limit while said vehicle is within said field of view, said processor identifying each vehicle for which said concentrations of said exhaust gases exceed said predetermined limits if said vehicle is determined to be in said hot state.

18. The system of claim 17 wherein said system is initially used to measure intensities of said infrared radiation and said visible light at a fixed location for a number of passing vehicles, and wherein said processor then calculates said first limit for infrared radiation and said second limit for visible radiation from said measured intensities for said passing vehicles by assuming that a predetermined statistical percentage of said passing vehicles are in said hot state.

19. The system of claim 17 further comprising optical chopper means for alternately blocking and unblocking said field of view of said infrared detector so that said infrared detector produces a signal that alternates between a reference value corresponding to darkness and a value corresponding to the intensity of infrared radiation from said field of view.

20. The system of claim 17 wherein said vehicle includes a front portion housing said engine, and wherein said field of view of said infrared detector includes a portion of said roadway adjacent to said front portion of said vehicle.

21. The system of claim 17 wherein said vehicle includes a side portion, and wherein said field of view of said infrared detector includes a portion of said roadway adjacent to said side portion of said vehicle.

22. The system of claim 17 wherein further comprising a camera aligned to record an image of each vehicle identified by said processor, including any vehicle identification material displayed on said vehicle.

23. The system of claim 22 wherein said camera comprises a video camera, and wherein said system further comprises video recording means for storing said vehicle image together with data regarding said concentrations of said exhaust gases measured for said vehicle.

24. A gas analysis system for remotely identifying moving motor vehicles on a roadway having concentrations of exhaust gases above predetermined limits, each of said vehicles having an engine and exhaust system components (the "components") that may initially be cold after said engine is first started (the "cold state") and that become hot after a period of operation (the "hot state"); wherein said components in said hot state emit substantially more infrared radiation than components in said cold state, with at least a portion of said infrared radiation being directed toward said roadway; said system comprising:

- a source for producing and transmitting a beam of radiation through at least a portion of the exhaust of a motor vehicle; and
- a plurality of sensors for receiving said beam, each sensor generating a signal indicative of the absorption of said beam in a wavelength band indicative of a corresponding one of said exhaust gases;
- an infrared detector for detecting infrared radiation within a field of view including at least a portion of said roadway beneath said vehicle;
- a processor responsive to said sensors for computing the concentrations of said exhaust gases in the path of said beam through said exhaust, and for determining whether said vehicle is in said hot state by measuring the intensity of infrared radiation detected by said infrared detector while said vehicle is within said field of view, said processor identifying each vehicle for which said concentrations of said exhaust gases exceed said predetermined limits if said vehicle is determined to be in said hot state;
- a camera aligned to record an image of each vehicle identified by said processor, including any vehicle identification material displayed on said vehicle; and
- storage means for storing said vehicle image together with data regarding said exhaust gas concentrations measured for said vehicle.

25. The system of claim 24 further comprising a visible light detector for detecting the intensity of visible light within a field of view that at least partially overlaps said field of view of said infrared detector, and wherein said processor determines that said vehicle is in said hot state if the intensity of infrared radiation detected by said infrared detector exceeds a first predetermined limit and the intensity of visible light detected by said visible light detector does not exceed a second predetermined limit.

* * * * *